(12) United States Patent
Auphan

(10) Patent No.: US 8,690,751 B2
(45) Date of Patent: *Apr. 8, 2014

(54) SLEEP AND ENVIRONMENT CONTROL METHOD AND SYSTEM

(76) Inventor: Raphael Auphan, Lyons (FR)

( * ) Notice: Subject to any disclaimer, the term of this patent is extended or adjusted under 35 U.S.C. 154(b) by 181 days.

This patent is subject to a terminal disclaimer.

(21) Appl. No.: 13/112,996

(22) Filed: May 20, 2011

(65) Prior Publication Data

US 2012/0296156 A1 Nov. 22, 2012

Related U.S. Application Data

(63) Continuation of application No. 12/419,273, filed on Apr. 6, 2009, now Pat. No. 7,967,739, which is a continuation of application No. 11/027,180, filed on Dec. 29, 2004, now Pat. No. 7,524,279.

(60) Provisional application No. 60/534,168, filed on Dec. 31, 2003.

(51) Int. Cl.
*A61M 21/00* (2006.01)

(52) U.S. Cl.
USPC .................................. 600/28; 600/26; 600/27

(58) Field of Classification Search
USPC ............................................. 600/26–28, 301
See application file for complete search history.

(56) References Cited

U.S. PATENT DOCUMENTS

| | | | |
|---|---|---|---|
| 5,101,831 A | 4/1992 | Koyama et al. | |
| 5,441,476 A | 8/1995 | Kitado et al. | |
| 5,902,250 A | 5/1999 | Verrier et al. | |
| 6,171,264 B1 | 1/2001 | Bader | |
| 7,366,572 B2 * | 4/2008 | Heruth et al. | 607/48 |
| 2001/0048639 A1 | 12/2001 | Davidson | |
| 2008/0167535 A1 * | 7/2008 | Stivoric et al. | 600/301 |
| 2010/0197996 A1 * | 8/2010 | Cornel | 600/28 |

OTHER PUBLICATIONS

Gaudreau, H., Carrier, J. and Montplaisir, J., Age-related modifications of NREM sleep EEG: from childhood to middle age (2001), Journal of Sleep Research, vol. 10, pp. 165-172.*

* cited by examiner

*Primary Examiner* — Jacqueline Cheng
*Assistant Examiner* — Eileen Foley
(74) *Attorney, Agent, or Firm* — Wiesner & Associates; Leland Wiesner

(57) ABSTRACT

A sleep system is provided that aids in achieving a sleep goal by controlling the environment near a person. The sleep system executes instructions on a processor that interfaces with the person and various environmental controls. As the instructions are executed, the sleep system receives a sleep goal for the person that includes varying the nearby environment. The processor may further execute instructions to create settings that vary at least one environmental condition of the environment over time as it relates to one or more cycles of a sleep architecture for the person. Varying at least one environmental condition near the person experiencing one or more cycles of the sleep architecture influences the quality of the person's sleep. The sleep system may further adjust at least one environmental condition in the vicinity of the person tailored to the sleep architecture for the person.

15 Claims, 6 Drawing Sheets

SLEEP AND ENVIRONMENT CONTROL METHOD AND SYSTEM

CROSS REFERENCE TO RELATED PROVISIONAL APPLICATIONS

This application is a continuation of and claims priority to U.S. Pat. No. 7,967,739 (application Ser. No. 12/419,273) by Raphael Auphan filed Apr. 6, 2009 entitled Sleep and Environment Control Method and System, which claims priority to and is a continuation of U.S. Pat. No. 7,524,279 B2 (application Ser. No. 11/027,180) also by Raphael Auphan filed Dec. 29, 2004 entitled Sleep and Environment Control Method and System, which in turn claims priority to U.S. Provisional Application Ser. No. 60/534,168 filed Dec. 31, 2003, all of the aforementioned patents and applications incorporated by reference in the entirety herein for all purposes.

BACKGROUND

A great deal of research in recent years has been focused on understanding sleep and its physiological and psychological effect on humans. While it is clear that humans require sleep to function properly, the qualities and quantities of sleep required is a much more complex problem. For example, some individuals that sleep too little may feel tired or fatigued during the day while other individuals that sleep too many hours have a similar feeling of grogginess as a result of sleeping too much. Researchers continue to study many different physiological conditions during sleep to understand the complex interplay between sleep and wakeful well-being.

To better analyze sleep, these researchers have broken sleep down into a framework or architecture having a series of cycles. One type of sleep architecture divides these cycles into REM (rapid eye movement) and Non-REM (NREM) types of sleep. A further classification divides the NREM sleep into: Stage 1 or Light Sleep—marked by a slowing in breathing and heart rate during the transition from waking and sleeping, Stage 2 or True Sleep—further identified with muscle relaxation, reduced or limited eye movement as well as body movement, Stage 3 or Deep Sleep Phase I—additional slowing of heart and breathing and Stage 4 or Deep Sleep Phase II—this is the deepest stage of sleep and arousal can be difficult. In contrast, REM stage or Dream Sleep is a separate type of sleep marked by a more distinct reduction in muscle tone and no body movement however breathing and heart rate may increase and become irregular; during REM eye movements are rapid as a person has vivid dreams.

Expensive computers and diagnostic equipment have been developed along with this research to identify these stages while a person sleeps. Sleep clinics located at hospitals and other medical research institutions admit patients briefly for one to two evenings for monitoring and analysis in order to diagnose sleep related illnesses and conditions like sleep apnea, insomnia, narcolepsy and other diseases. Medical doctors carefully review vital signs and other information collected from the person during sleep in an attempt to diagnose the specific conditions having a deleterious effect on the person's health and well-being. Due to the costs and business-like nature of medicine, doctors not only diagnose but often suggest medical procedures, prescription drugs and/or medical devices based on the data gathered during these abbreviated sessions. In minor cases, a doctor may prescribe a sedative or other drug to alleviate stress and induce sleep while in the more severe cases the doctor may also recommend medical devices to address specific conditions (i.e., a mask and breathing apparatus for sleep apnea) and perform radical and painful surgery involving the throat, nasal cavities, tongue and respiratory tract.

Drugs and surgical procedures not only represent risks but are often ineffective at treating sleep disorders. This is not surprising given the limitations and imperfections in monitoring and treating sleep disorders. First, the monitoring done in hospitals is expensive and typically available only near large universities and research institutions. As a result, data collected does not reflect a cross-section of society or a broad range of people but instead represents only those people near the sleep clinics and/or with sufficient insurance and financial resources to pay for the work. The resulting sleep data available is therefore limited and potentially too small to be considered statistically significant.

Further, data collected during these one or two night stays are often too short and unpredictable to make accurate assessment of problem. For example, a person sleeping in a clinic with numerous monitoring devices and other equipment may be uncomfortable and exhibit additional sleep problems. Any information gathered over the short period of time in a sleep clinic may reflect the person's discomfort sleeping in a clinic with numerous monitors rather than displaying the symptoms of a true sleeping disorder (i.e., sleep apnea, narcolepsy, etc.)

Current sleep research also does not address the more subtle sleep problems suffered by the majority of people as the focus has been more of a last resort for people with severe sleep conditions. If it were possible, many people could benefit from sleep research if it were available more widely and inexpensively.

SUMMARY

One aspect of the invention includes a sleep modification method that includes receiving a sleep goal that may be achieved through control of an environment near a person. Implementations of the present invention may create settings that vary at least one environmental condition of the environment over time as it relates to one or more cycles of a sleep architecture for the person. Varying the at least one environmental condition near the person over time influences a sleep quality of the person experiencing one or more cycles of the sleep architecture.

Another aspect of the present invention also includes a sleep modification method that includes receiving a sleep goal that may be achieved through control of an environment near a person. In these implementations, the method creates settings that vary at least one environmental condition of the environment over time as it relates to one or more cycles of a sleep architecture for the person. These settings influence a sleep quality of the person through control of the at least one environmental condition near the person experiencing one or more cycles of the sleep architecture. Additionally, implementations of the present invention may adjust the at least one environmental condition in the vicinity of the person in accordance with the sleep architecture for the person.

Yet another aspect of the present invention includes a sleep system that aids in achieving a sleep goal through the control of an environment near a person. The sleep system includes a processor capable of executing instructions used for controlling one or more aspects of the environment and a memory capable of holding the instructions. Upon executing the instructions, the sleep system receives a sleep goal for the person achievable through control of the nearby environment. The processor may further execute instructions to create settings that vary at least one environmental condition of the environment over time as it relates to one or more cycles of a sleep architecture for the person. Varying at least one environmental condition near the person experiencing one or more cycles of the sleep architecture influences the quality of the person's sleep. The sleep system may further adjust at least one environmental condition in the vicinity of the person in accordance with the sleep architecture for the person.

Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
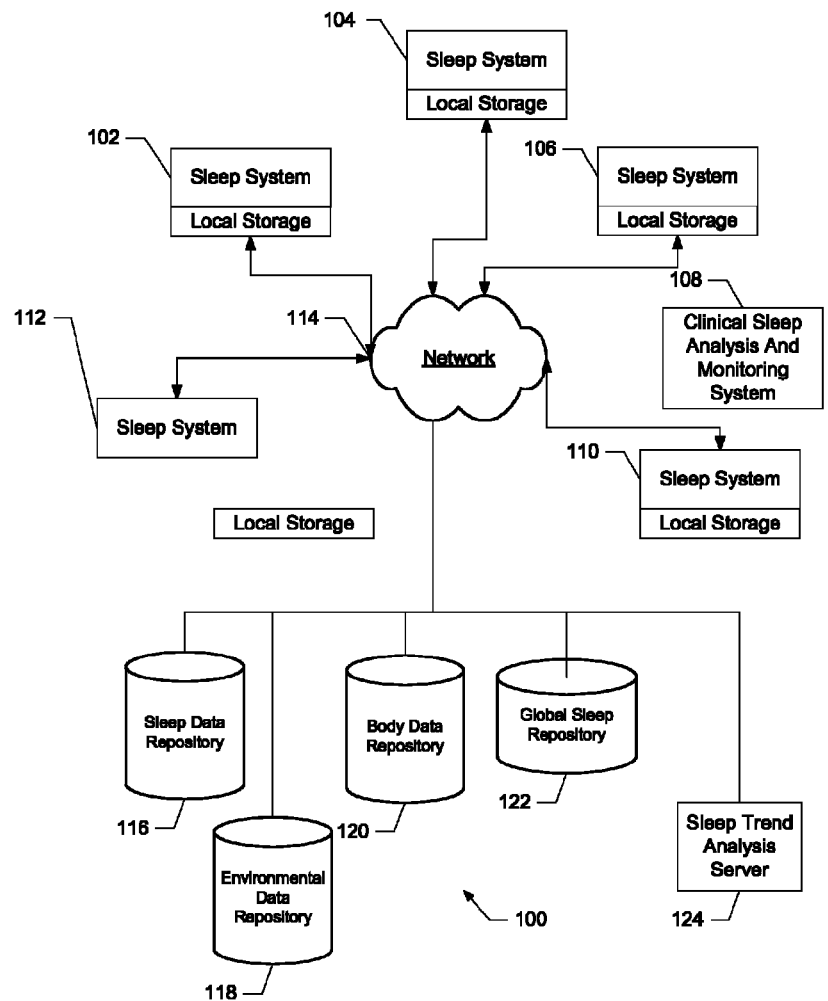
FIG. 1 depicts a network of sleep systems and servers for sleep analysis and modification in accordance with one implementation of the present invention.

Aspects of the present invention include a sleep system for monitoring sleep and controlling the environment where a person is sleeping. Numerous sensors built into the sleep system gather data from the person and the environment and then process the information to identify trends and sleep quality for the individual. Historical sleep data for the person is stored in a local repository and used during sleep analysis as well as an optional global sleep repository with the sleep data for many individuals. Depending on the individual's goals, the sleep system is adjusted causing subtle changes in the environment (i.e., sound, light, heat/cooling, vibration etc.) to improve and meet these goals related to sleep and overall health.

While there are many different advantages not all of which are specifically identified herein, one or more aspects of the present invention may include one or more of the following advantages. A sleep system and related processing can be implemented as easily in a person's home as a clinical or hospital setting. The sleep system is designed to monitor sleep patterns and sleep quality of a person without requiring expertise or training in sleep analysis and diagnosis. Built in sensors and feedback loops in the system monitor a person's body and environment and then use sophisticated computer implemented data analysis routines to modify the environment and improve the person's sleep. By collecting sleep data from the person in a local sleep repository over a period of time, the sleep patterns for the person can be readily detected and accommodated with customized stimulus most suited for the individual. If it is desired, the person can also connect to a global sleep repository and use sleep data from larger groups of individuals to help determine optimal sleep settings for their particular sleep system and sleep condition.

Multiple objective, subjective and environment factors are used in combination to evaluate a person's sleep. Sensor inputs recording vital signs of a person during sleep are combined with environmental sensor information to provide a context or baseline for the person's sleep analysis. If environmental sensor information is not available or desired then objective factors related to a person's vital signs can alternatively be used without the environmental information. Additional factoring in of subjective information gathered from each person concerning their perceived condition before, during and after sleep helps tailor the analysis to each individual. These many different factors help facilitate a more accurate assessment and improvement of a person's sleep.

Longer term data collection and sleep trend analysis is possible with implementations of the present invention. Instead of being limited to one or two hours or nights in a sleep clinic or hospital, sleep systems installed in a home setting can gather data over days, months or even years. False readings due to uncomfortable sleep situations or monitoring devices can eventually be identified and factored out over time. These additional data points describing a sleep condition over a longer period of time help customize the analysis and develop more accurate models of a person's sleep patterns and cycles. More can be learned about sleep over time as the sleep data is collected and compared with larger populations of people.

FIG. 1 depicts a network of sleep systems and servers for sleep analysis and modification in accordance with one implementation of the present invention. System 100 includes sleep systems 102, 104, 106, 110 and 112 coupled together over a network 114 such as the Internet. Additionally, system 100 also includes a clinical sleep analysis and monitoring system 108 and sleep trend analysis server 124 both capable of accessing data stored in sleep data repository 116, environmental data repository 118, body data repository 120 and global sleep repository 122.

Sleep systems 102, 104, 106, 110 and 112 are designed to gather sleep and body data from individuals as they are sleeping as well as environmental data surrounding the sleep systems. For example, sleep system 102 gathers body and sleep related information and environmental data and stores in a local storage area to be accessed later during an analysis phase. The body information typically includes vital signs measured directly from the person during the sleep cycle and includes the time period before falling asleep as well as the time period while asleep and the period following when the person wakes up. In addition to having a variety of sensors, the sleep system includes various computer processing devices and controls outputs for controlling the environment. Optionally, these various devices can be integrated into a bed and other bedding or can be added to any existing bed or bedding as described in further detail later herein.

Clinical sleep analysis and monitoring system 108, hereinafter clinical monitoring system 108, is an optional component available for use by each sleep system user as an additional service. While implementations of the present invention can readily work as a standalone device, in some cases, a person may desire that they need special assistance monitoring and diagnosing their sleep. These people would pay according to a monthly, annual or other fee schedule for a qualified sleep specialist, medical doctor or researcher to monitor and respond to certain sleep conditions. If a person or system at clinical monitoring system 108 detects an issue with respect to a person's sleep then they will contact the individual and notify them of the anomalous condition. In response, the personnel at the monitoring service can directly adjust the environmental settings or modify the settings of the sleep system over a remote link in order to improve the sleep quality of the person. Conversely, the person using one of the sleep systems may opt not to use clinical monitoring system 108 and instead rely on the analysis, modeling and trend analysis functions already built into the sleep system designed in accordance with the present invention.

Sleep trend analysis server 124 and various sleep repositories represent yet another optional service available to each user of a sleep system. Instead of working with data related to a specific individual, sleep trend analysis server 124 can perform analysis on large populations of people using sleep systems of the present invention. Participating sleep systems 102, 104, 106, 110 and 112 can opt-in to populate each of sleep data repository 116, body data repository 120 and environmental data repository 118 with information gathered over time. In exchange, these participating sleep systems 102, 104, 106, 110 and 112 have access to a wider range of information and sleep system setting suggestions and options other than from the individual local storage database.

The datasets associated with sleep data repository 116 include information directly related to sleep quality. For example, sleep related information may include a number of wakeups during sleep time, duration of these wakeups during sleep time and other types of related information. Environmental data repository 118 stores details on the environment before, during and after sleep time while body data repository 120 retains more specific information concerning vital signs and other details of the individual person as they sleep. Of course, these repositories are cross referenced using various indices and/or can be combined into a single larger repository if so desired.

Global sleep repository 122 holds the results of trend analysis performed by sleep trend analysis server 124 on these above mentioned repositories (i.e., sleep data repository 116, body data repository 120 and environmental data repository 118). One objective of the trend analysis is to determine one or more optimal sleep system settings for each of sleep systems 102, 104, 106, 110 and 112 under various circumstances. Due to the complexity of identifying an optimal solution, one or more techniques implemented by sleep trend analysis server 124 relies upon various heuristics and solution methodologies for solving other N-P complete problems including: genetic programming techniques, tree-based modeling solutions and artificial intelligence analysis. As described in further detail later herein, a sleep quality index and corresponding set of sleep system settings generated by sleep trend analysis server 124 are made available on demand to one or more of the sleep systems in network 100.

Figure 2:
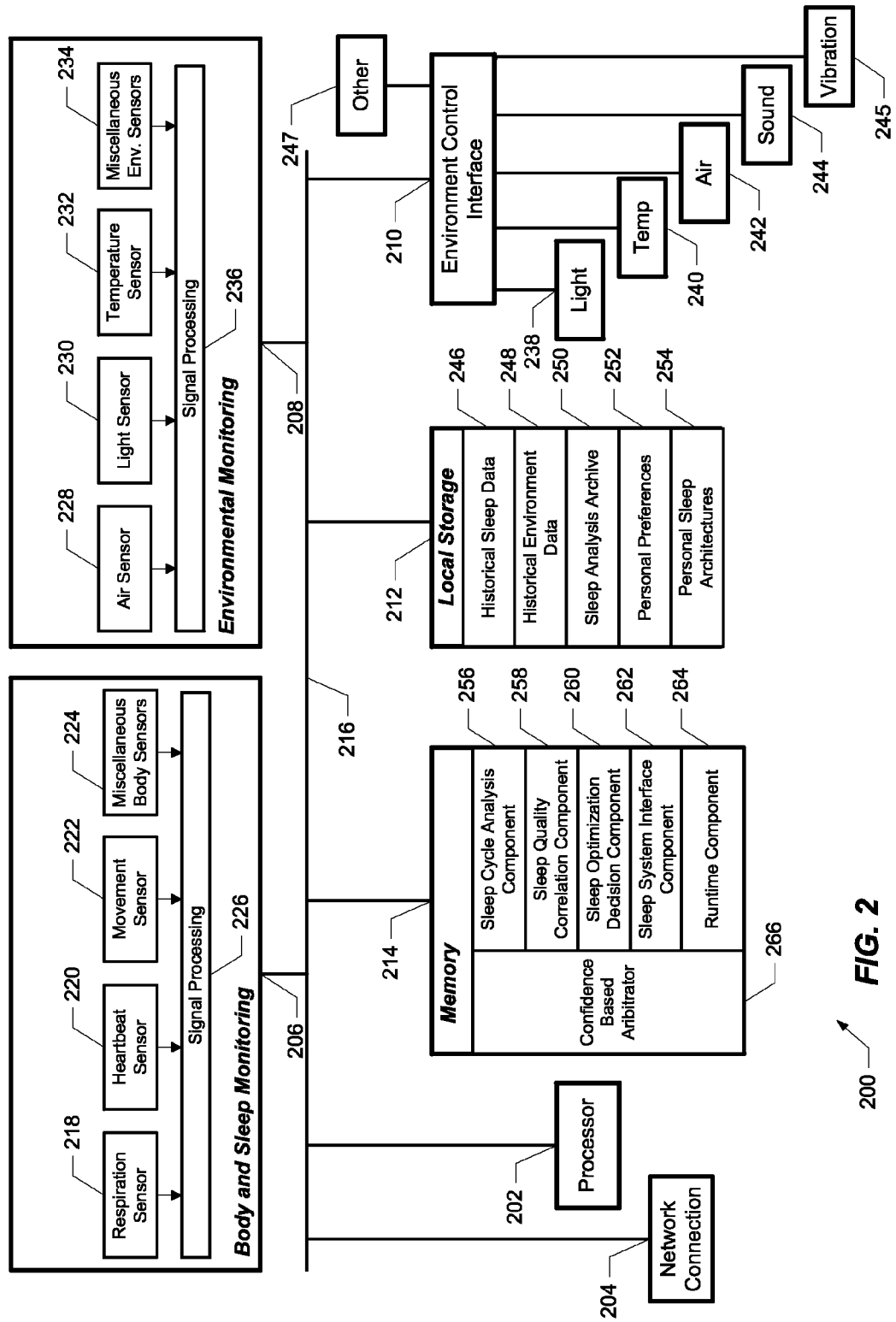
FIG. 2 depicts components of a sleep system used for analysis and modification of sleep in accordance with one implementation of the present invention.

FIG. 2 depicts components of a sleep system used for analysis and modification of sleep in accordance with one implementation of the present invention. As illustrated in this example, sleep system 200 includes a processor 202, a network connection 204, a set of body and sleep monitoring sensors 206, environmental monitoring sensors 208, an environmental control interface 210, local storage 212 and memory 214. Alternate implementations of the present invention may include fewer than all of these options as needed by the specific design. For example, a standalone sleep system 200 may not include network connection 204 if communicating with other devices, sleep systems or data storage is not needed.

Processor 202 can be one or more general purpose processors arranged to process instructions in parallel or in a cluster arrangement. Alternatively, processor 202 can also include a set of special purpose embedded processors designed to work together on specific processing tasks associated with sleep analysis and modification as needed by implementations of the present invention. Network connection 204 provides connectivity to an intranet or the Internet and access to larger repositories or databases of sleep data and information as previously described. This network connection 204 can also be used to download updates to applications or firmware within sleep system 200 as well as provide the ability to provide remote monitoring and/or remote diagnostics on sleep system 200 and/or the person.

Body and sleep monitoring sensors 206 provide an interface and sensors for gathering vital signs and other information about the person as they fall asleep, sleep and then wakeup. In one implementation, these body and sleep monitoring sensors 206 include a respiration sensor 218 to measure breathing rate and gas mixture (VO2 levels), heartbeat sensor 220 to measure heart rate, heart rate variability and pulse, movement sensor 222 to measure body movement and various other miscellaneous body sensors 224 useful in sleep analysis. To minimize the impact on sleep, these sensors should be designed to collect data non-invasively however alternate implementations of the present invention will also work with more invasive devices that touch or are placed upon the person. These various sensors are fed into a signal processing component 226 to filter and digitize the various results and prepare for further analysis.

A different set of sensors in environmental monitoring sensors 208 include: an air sensor 228 for measuring air temperature and quality, a light sensor 230 for measuring the intensity and frequency of the light in the environment, a temperature sensor 232 that measures ambient room temperature and various other miscellaneous environmental sensors 234 as needed by the sleep analysis performed in accordance with the aspects of the present invention. For example, one environmental sensor 234 could include a sound sensor to detect and measure certain sound levels and frequencies.

Environmental control interface 210 sends different control signals out depending on sleep analysis results from the sensor data, historical data and other inputs as described later herein. These control signals cause various conditions in the environment to change with the desired effect being to influence and improve the sleeping quality of the individual person sleeping or about to sleep in the particular environment. In one example implementation as illustrated, the control signals from environmental control interface are capable of interfacing and controlling one or more of the following environmental conditions: light 238 (intensity and color), temperature 240 (both temperature at sleep surface as well as surrounding areas), air 242 (volume, humidity, gas composition, scents and temperature) 242, sound 244 (volume, frequency and timbre), vibration 245 and many others 247. For example, environmental control interface can also interface with audio/video equipment and devices for playing movies, music and sounds. In many cases, the desired environmental condition depends on the sleep cycle a person is in (i.e., light sleep, deep sleep, REM/dream sleep) or going into and may need adjusting accordingly depending on their preferences and particular sleep cycle architecture.

Local storage 212 is a dataset storage area for storing data collected from the sensors, and data processed/analyzed by the system as well as subjective information collected from the person. As previously described, this information can be kept locally and/or can be transmitted to one or more global repositories to be stored along with sleep information from many other people. Historical sleep data 246 includes raw and processed data describing the person's actual sleep characteristics over a period of time. In many cases, the historical sleep data 246 is inferred directly from data taken from one or more of the various sensors. For example, the number of wakeups and corresponding duration of wakeups can be determined based upon movement data collected from movement sensor 222 in addition to other vital signs taken from the various other vital signs measurements. Historical environment data 248 is also a collection of raw data taken over time except it concerns environmental information obtained directly through environmental monitoring sensors 208 as previously described.

Sleep analysis archive 250 is a collection of sleep analysis results performed over time and kept for future reference. The sleep analysis results in sleep analysis archive 250 are derived by identifying trends in past data and information collected by the various sensors in sleep system 200 and through subjective feedback provided by the person after a sleep.

Personal preferences 252 include preferred settings for each person using sleep system 200. These preferences in personal preferences 252 can be changed quickly to accommodate multiple people using sleep system 200 without requiring reprogramming or retraining. For example, the preferences can specify a modified and personal sleep architecture 254 that has been modified to suit a particular user. Personal sleep architectures 254 describe classical stages of sleep tailored to each individual person. For example, a sleep architecture having stage 1 (light sleep), stage 2 (true sleep), stage 3/4 (deep sleep) or delta sleep and REM stage (dream sleep) may also indicate more specific time intervals for each depending on the historical analysis of sleep for the individual. Additional preferences included in personal preferences 252 can also include air temperature range settings not to exceed or heart rate and blood pressure threshold levels to set off warnings or other emergency procedures.

A number of example components useful in sleep and sleep quality analysis are illustrated in memory 214 including: a sleep cycle analysis component 256, a sleep quality correlation component 258, a sleep optimization component 260, a sleep system interface component 260 and a runtime component 264 for managing the resources in memory 214 and other parts of sleep system 200.

Sleep cycle analysis component 256 analyzes sensor information, environmental information and subjective information from the person and constructs a more accurate sleep architecture for the individual. This can involve adjusting the times associated with each cycle of the sleep architecture as well as drawing a correlation between the data from one or more sensors and the particular person's entry or exit from the different cycles. For example, sleep cycle analysis component 256 may also include analyzing the effectiveness of past wake-up times and then setting a more optimal wake-up time based upon the persons and desired wake-up time frame (i.e., if the desired wakeup period is between 6 am and 7 am, the system may analyze the sleep data gathered during the night and determine that the most optimal wakeup time would be 6.15 am).

Once the sleep cycle architecture is known for each person, sleep cycle analysis component 256 is also responsible for developing an objective measure of sleep quality through analysis of the sensor data from the person and, optionally, from the environment. Objective measures of sleep quality in one implementation are based upon factors that include: sleep inertia after waking up, sleep debt accumulation, architecture of sleep phases, breathing quality, sleep efficiency, duration of wakeups during sleep time, actual frequency of wakeups, sleep onset time, wake-up time, total sleeping time and actual time taken to fall asleep. If it is desired these objective factors related to the body and sleep of the person can also be combined with environmental sensor information results as previously described and collected via environmental monitoring sensors 208.

Sleep quality correlation component 258 combines an objective measure of sleep quality with subjective measurements of sleep quality obtained from the person and generates a sleep quality index. The sleep quality index is a weighted combination of the objective and subjective measures of sleep quality. In some cases, the sleep quality index may also be normalized to allow a personal sleep quality index to be compared with the sleep quality index of other people. Correlations are generally made using both current and historical sleep quality index values as they relate to sleep system settings. Depending on the type of analysis, it may also be useful to combine environmental data in these correlation calculations. Many times environmental factors have a noticeable effect on a person's sleep and therefore justify performing additional computations and correlative analysis.

It is contemplated that the subjective factors are generally obtained shortly after a person wakes up and are based primarily upon the person's perception of the sleep. In some cases, these perceived measures of quality may match the more objective measures taken through sensors while in other cases they may not match up. In any event, implementations of the present invention consider and weight the subjective factors in light of their consistency over time rather than whether they identically track or closely track other measures or results taken using sensors. These subjective measures of sleep quality include: body comfort, stress level on wakeup, stress level to sleep, perceived somnolence during day, recall of dreams, frequency of wakeups recalled, perceived time to fall asleep, overall perception at wake-up and overall perception of sleep quality.

In practice, a person using sleep system 200 might enter these subjective measures of sleep quality through a small remote control having a touch screen and capable of scrolling various multiple choice and other questions in front of the person after waking up. Sleep system interface component 262 would likely have a set of screens available for the creation and procuring of subjective measures of sleep quality from the person. The results of these enquiries would be forwarded over a wireless or wired connection to sleep system 200 for further analysis and consideration.

Additional functions performed through sleep system interface component 262 can also include setting up personal preferences 252 and any additional alerts or alarms to be set upon reaching certain threshold conditions (i.e., low oxygen intake, high blood pressure, slowed or stopped breathing etc.) One personal preference 252 can request sleep system 200 to identify certain sleep patterns and then suggest one or more modifications to the person for improving sleep based on collected sleep information and analysis. An expert system designed to analyze sleep patterns and make suggestions allows the user to take control of certain aspects of sleep system 200 without having to understand and analyze all the details. For example, sleep system 200 may notify through sleep system interface component 262 a certain time during sleep when a person is restless and moving about. Using an expert knowledgebase of information on sleep, sleep system 200 also might then suggest either a temperature increase, increased oxygen flow or some other intervention to address the specific condition. The person would be able to select one of these responses to perform by sleep system 200 as a preference next time the condition occurs. Of course, the person can also override the expert system and directly instruct sleep system 200 to operate in a certain manner upon occurrence of almost any detectable event.

Sleep optimization decision component 260 and confidence based arbitrator 266 work together in determining how to improve the person's sleep experience. In one implementation, sleep optimization decision component 260 receives sleep analysis information from sleep cycle analysis component 256 and sleep quality correlation component 258 and determines whether to adjust the settings of sleep system 200. In some cases, the basis for these decisions depends entirely on historical sleep and environmental information stored in local storage 212 while in other cases additional historical sleep information is obtained from other people and correlated with their corresponding sleep quality index and sleep system settings. If the trend for changing the sleep system settings is clear then sleep optimization decision component 260 sends signals over environmental control interface 210 as appropriate to alter the environment.

However, if it is unclear what changes in sleep system 200 are needed or there is a deadlock then confidence based arbitrator 266 acts as a secondary decision maker in the process. For example, analysis by sleep optimization decision component 260 may result in a conflicting set of instructions to increase air temperature and simultaneously lower air temperature. Confidence based arbitrator 266 would determine which of the decisions is more likely to be correct based on confidence based factors and then choose one decision over the other to break the deadlock.

The organization of data in local storage 212 and the components described above in memory 214 represents only one possible solution and it is contemplated that each of these datasets and components could be combined with other datasets or components or separated into a further larger number of datasets or components depending on the design decisions and choices made during implementation. Further, while the components are illustrated in this example as appearing in main memory of a device however they could also be loaded and run from local storage 212 on a disk drive or removable memory/storage (not shown). In addition, data in local storage 212 and components in memory 214 could instead be mastered onto a DVD or CD-ROM. Accordingly, these components are illustrated in memory as one example approach to process these instructions.

Figure 3:
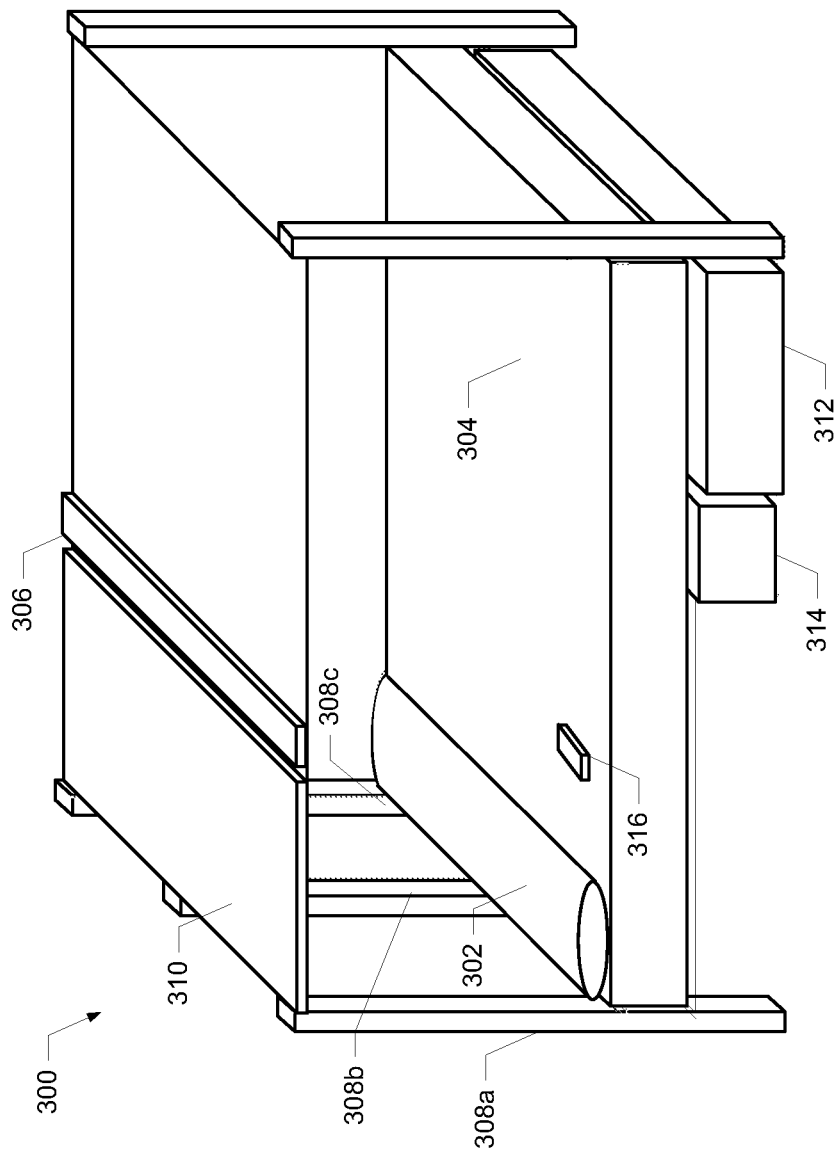
FIG. 3 depicts a sleep system with sensors and controls integrated into a bed in accordance with one implementation of the present invention.

FIG. 3 depicts a sleep system with sensors and controls integrated into a bed in accordance with one implementation of the present invention. The sleep system 314 in this example is designed into and integrated with a complete bed. Accordingly, bed system 300 includes a sensor pillow 302, sensor fitted bed sheet 304, overhead monitors 306, integrated air ducts 308a-c, multimedia area 310, air processing unit 312, sleep system 314 and sleep user control device 316.

Sensor pillow 302 and sensor fitted bed sheet 304 are used primarily to obtain various measurements from the person sleeping. These measurements taken from the person are made through various sensors including, for example, respiration sensors, heartbeat and blood pressure sensors, EEG (electroencephalogram) sensors, ECG/EKG (electrocardiogram) sensors, movement sensors and body temperature sensors. As measurements are made they are immediately transmitted to sleep system 314 for storage and subsequent or immediate processing.

Overhead monitors 306 include sensors used primarily in sampling the environment and determining, among other things, air temperature and quality, light intensity and frequency in the environment, ambient room temperature and various other environmental qualities as needed. Additionally, cameras, video cameras and infrared cameras can be included in overhead monitors to monitor the persons movements and behavior during sleep. These measurements are also sent immediately to sleep system 314 for storage and processing.

Depending on the sleep cycle, one or more environmental controls in bed-system may be activated or altered. Integrated air ducts 308a-c can be adjusted to intake and exhaust air as needed to effectuate a more improved sleep condition for the person. For example, the air flow could be increased to either increase or decrease temperature as well as potentially increase the level of oxygen in the sleeping area (e.g., either by increasing the overall air flow or by actually increasing the percentage of oxygen in the air mixture). Additional air ducts may also be included in multimedia area 310 as needed.

Positioned just over the eyes of the person sleeping, multimedia area 310 includes lights, sound speakers and optionally an image producing screen (i.e., LCD or plasma) to project certain soothing images or patterns. Lights in multimedia area 310 can be controlled to permit reading before sleep or viewing of tranquil scenes or favorite images/patterns. Different patterns can be displayed and may have different effects on the person depending on their experiences and viewpoints. For example, mountain scenery may provide a peaceful feeling for some individuals or feelings of fear for people afraid of heights.

In this example, the air processing box unit 312 and sleep system 314 are located just underneath the bed however it is also possible they are located at an additional distance from the person sleeping. For example, it may be desirable to have air processing unit 312 located remotely to reduce ambient noise levels and also provide additional storage opportunities in the bedroom or sleeping area. Similarly, sleep system 314 can be located centrally to several rooms in a house to allow for the monitoring and control of several bed-systems 300 at once.

Sleep control device 316 is used by the person sleeping to turn bed system 300 on and off as well as interface and program the system as needed. As previously mentioned, sleep control device 316 can be equipped with a touch screen and may even include a small embedded web browser compatible with HTML/XML and other web based interface programming protocols. Alternatively, the person can operate sleep control device 316 using the buttons and/or touch screen elements to then browse one or several web pages displayed upon a display in multimedia area 310.

Figure 4:
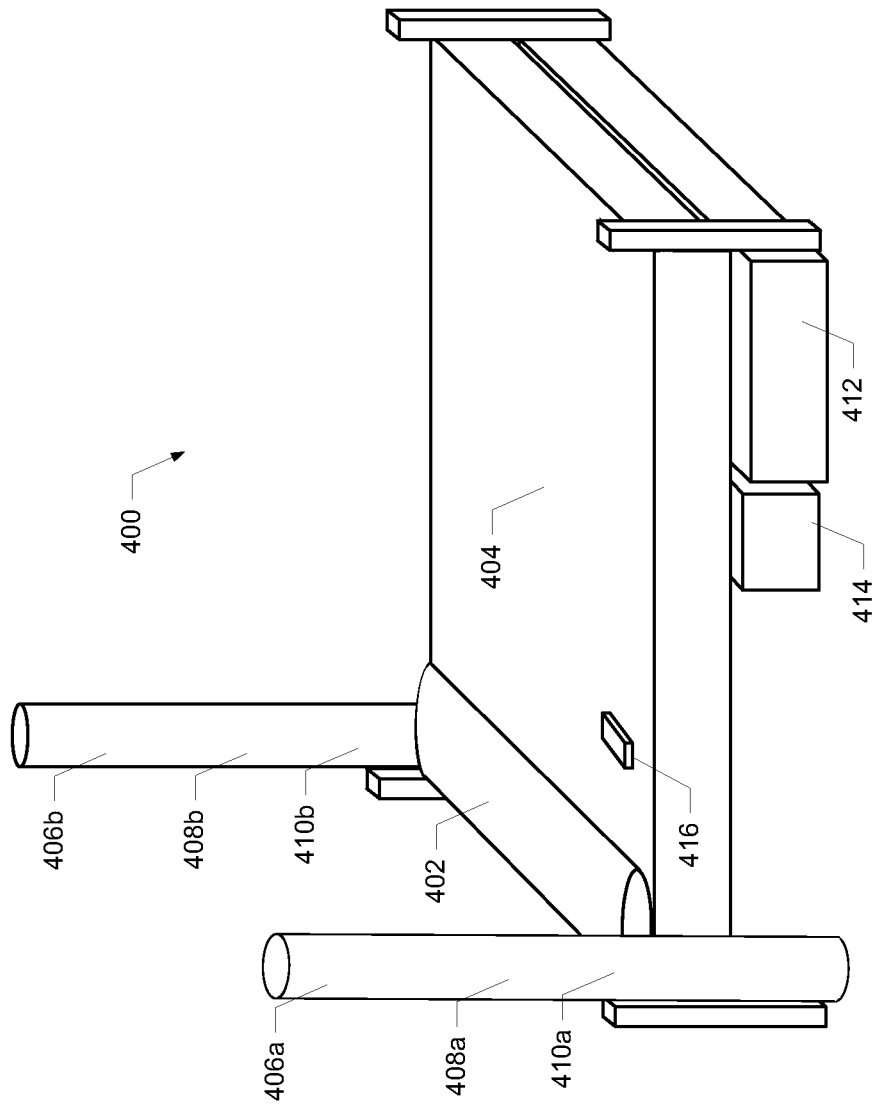
FIG. 4 is another bed having a sleep system designed in accordance with the present invention added afterwards rather than being integrated as previously described in conjunction with FIG. 3.

FIG. 4 is another bed having a sleep system designed in accordance with the present invention added afterwards rather than being integrated as previously described in FIG. 3. In this example, a bed 400 is modified by adding sensor pillow 402 and/or sensor fitted bed sheet 404 that operate as previously described with respect to similar sensors in bed system 300. Instead of overhead, a pair of side monitors 406a-b includes sensors that work together in sampling the environment and determining, among other things, air temperature and quality, light intensity and frequency in the environment, ambient room temperature and various other miscellaneous environmental conditions as needed. Once again, these measurements are sent immediately to sleep system 414 for storage and processing. Air intake and exhaust ducts 408 a-b and pair of multimedia areas 410a-b are also located on the sides and operate in a similar manner as the corresponding functional elements described with respect to bed system 300 in FIG. 3. Likewise, air processing unit 412, sleep system 414 and sleep control device 416 have similar function and operation as previously described in FIG. 3 as well. In this case, sleep control device 416 has a screen to display information and a touch screen to make selections unless an external screen/monitor (not shown) is plugged into sleep system 414 and used to guide the selection of options and preferences.

Figure 5:
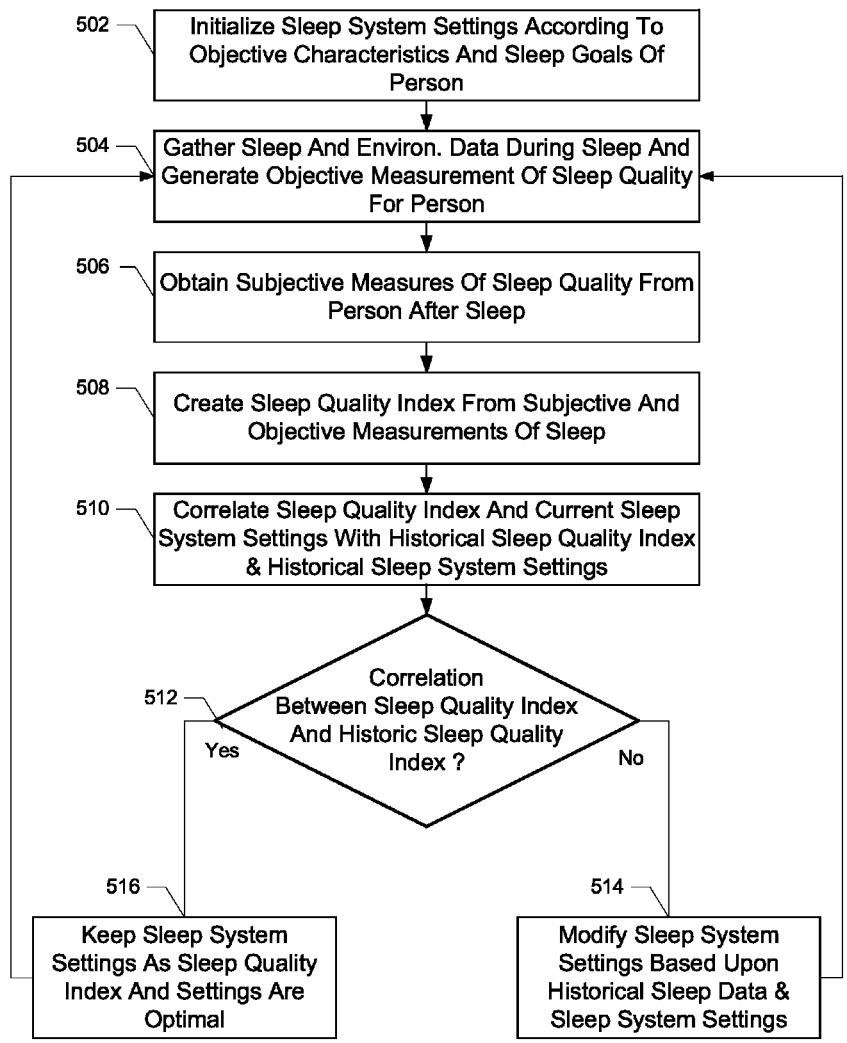
FIG. 5 is a flowchart diagram of the operations used to modify a person's sleep in accordance with one implementation of the present invention.

FIG. 5 is a flowchart diagram of the operations used to modify a person's sleep in accordance with one implementation of the present invention. Upon first use or initial use, a person may specify their objective characteristics and sleep goals to the sleep system (502). The objective characteristics may include sex, age, weight, relative fitness and other information readily quantified by the person about to use the sleep system. Sleep goals can be provided by selecting one of several or many options that may include: quicker time to fall asleep, deeper REM sleep, fewer wakeups during sleep, longer sleep times, more efficient sleeps or other types of sleep goals.

Next, the sleep system begins to gather environmental data during a sleep by a person and sleep data from the person and to generate an objective measure of sleep quality (504). Generally, the environmental data is not required to generate the objective measure of sleep but useful in drawing correlations between the sleep data from the person and the environmental factors as they occur. In one implementation, the objective measures of sleep quality include: sleep inertia after waking up, sleep debt accumulation, architecture of sleep phases, breathing quality, sleep efficiency, duration of wakeups during sleep time, actual frequency of wakeups, sleep onset time, wake-up time, total sleeping time and actual time taken to fall asleep. While sleep inertia is considered an objective measure of sleep, it can be measured by asking the person to perform a very basic test or skill to determine the level of alertness after wakeup as direct measurement is more difficult. If the person wakes up numerous times then the time taken to fall asleep in each instance is also recorded and preferably minimized when it does occur. The typical time taken to fall asleep is measured from the time the lights are out to the time the person experiences the onset of sleep. Over time, the sleep system provides suggested times to fall asleep and may also run various light and sound programs to assist in this process.

Once the person has awoken from sleep, the sleep system then enquires for a subjective measure of sleep quality (506). This measure of sleep quality is largely based upon the person's perception and helps the sleep system learn what type of sleep and settings in the sleep system makes the person feel more rested. Typically, the person enters these subjective factors through the sleep control unit and/or a visual graphical user interface (GUI). The subjective factors provided generally concern overall body comfort, stress level on wakeup, stress level to sleep, perceived somnolence during day, recall of dreams, frequency of wakeups recalled, perceived time to fall asleep and overall perception of sleep quality. Sleep inertia is also considered a subjective factor and measured upon wakeup by asking the person about their perceived sleep inertia or grogginess upon wakeup.

To account for both the objective and subjective measurements of sleep quality, the sleep system then creates a sleep quality index from the objective measurement of sleep quality and subjective measurement of sleep quality (508). In one implementation, this sleep quality index is a weighted combination of both the objective and subjective measurements of sleep quality. It may be important to normalize this sleep quality index in order to compare the index and sleep system settings with the indices and sleep system settings of other people using the sleep system. For example, a sleep quality index (SQI) can be computed as follows:

$$SQI = W_s \cdot \sum_{ST=x}^{m} \text{Subjective Sleep } Quality_{ST} + W_o \cdot \sum_{OT=y}^{n} \text{Objective Sleep } Quality_{OT}$$

Where:
$W_s$ is weight attributed to subjective sleep quality factor
$W_o$ is weight attributed to objective sleep quality factors
m is the number of subjective sleep quality samples
n is the number of objective sleep quality samples
x is the starting sample for subjective sleep quality measurement
y is the starting sample for the objective sleep quality measurement The sampling for the subjective factors and objective factors is performed at the highest rate possible to allow for many different types of analysis. Generally, the sampling for the subjective sleep quality is performed upon waking as it requires the person to be awake and provide information. For example, this sampling rate would typically be once a day in the morning when a person wakes up and the number of samples would therefore correspond to the number of days included in part of the analysis. The subjective sleep quality for a one month period would necessarily included 30 samples of subjective sleep quality while analysis for a 2 week period might only include 10-14 samples. Of course, many more subjective sleep quality samples are also possible if a person sleeps and wakes up several times a day.

Objective sleep quality can be measured at a much higher frequency as it does not necessarily require the person sleeping to be awake and respond. While these samples can be performed on a daily basis, it is contemplated that they would more likely be performed as frequent as several times a second or as much as once every 15 minutes or so to keep the data collection to a reasonable level. The more rapid collection of objective sleep quality allows the sleep system to react more rapidly or instantaneously to certain conditions if it is desired.

For example, the sleep system can monitor the objective sleep quality in real-time during sleep and automatically adjust one or more aspects of the sleep system as soon as certain sleep conditions are detected. If during sleep the person begins to wake or experience other changes in sleep behavior the sleep system has the ability to both detect this condition and then automatically readjust the sleep system settings to put the person back to sleep or at least improve the immediate sleep condition. Given the different sampling rate possibilities, it is possible that a different number of samples would be used in the subjective sleep quality measurement as in the objective sleep quality measurement provided they have some correlation to each other based on time or timing within a sleep cycle. For example, one or more subjective sleep quality measurements taken in the past can be used and reused in combination with different objective sleep quality measurements taken multiple times while a person is currently sleeping. Alternatively, the sleep system can be configured to match each subjective sleep quality sample with a corresponding objective sleep quality sample taken at or about the same time interval. The subjective sleep quality sample taken once a day would be matched up with an objective sleep quality sample also taken once a day at or about the same time interval.

The sleep system then correlates the sleep quality index and current sleep system settings with historical sleep quality indices and corresponding historical sleep system settings (510) and identifies a trend. By examining past sleep quality indices, the sleep system is able to determine if a better group of settings would more likely or less likely to create a more effective environment for achieving certain sleep quality for the person. For example, a certain pattern of lights or music may be effective at increasing a person's time to sleep and/or may decrease the overall number of wakeups during sleep. Once asleep, a dim light left on may help reduce the reoccurrence of wakeups or at least reduce their effect and decrease the time to fall back to sleep after a wakeup.

The sleep system modifies the sleep system settings depending on the correlation between the sleep quality index and the historical sleep quality indices in the system (512). If the proper correlation between the current sleep quality index and the historical indices is discovered then the current sleep system settings are kept as the sleep system settings are already set to an optimal level (516). However, a divergence between the current sleep quality index and settings compared with the historical sleep quality indices and settings may indicate a different set of sleep system settings is more appropriate (512). Accordingly, implementations of the present invention would then modify the sleep system settings based upon the historical sleep quality indices, data and sleep system settings (514). For example, a modification may include changing the temperature of the environment and providing a dim light during sleep to counteract wakeups or other undesirable sleeping pattern or behavior. As previously described, the sleep system can make these changes as rapidly as the sampling rate for the objective sleep quality measurements permit or can be fixed prior to sleeping and adjusted once a day after waking or on even a more infrequent basis.

Figure 6:
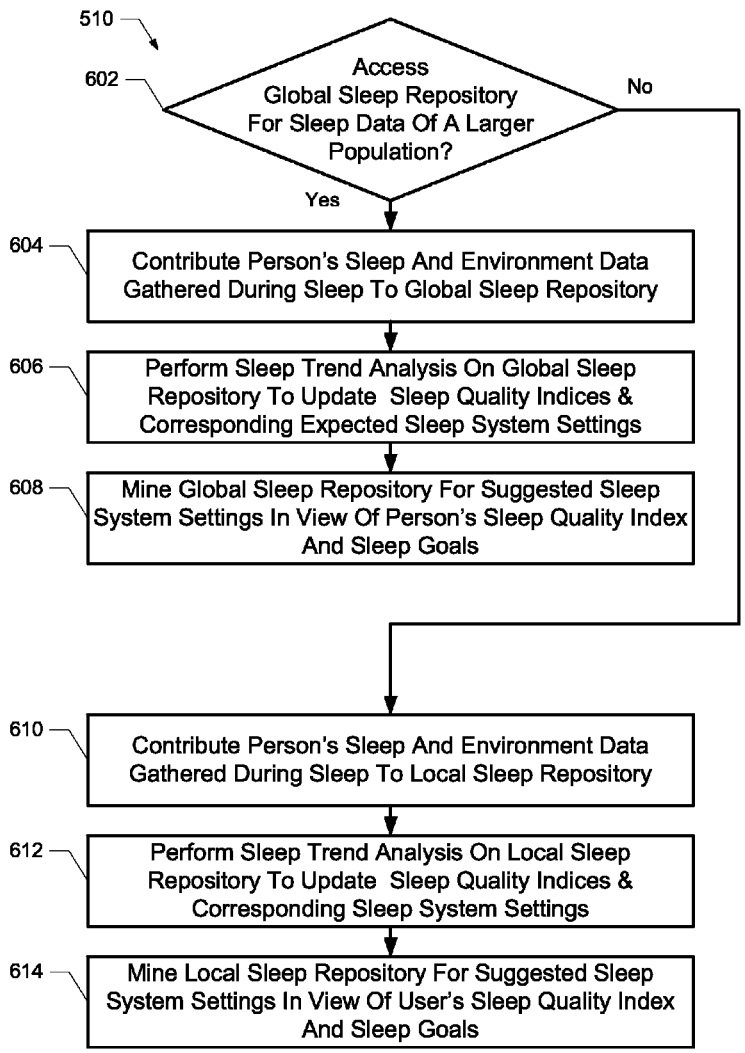
FIG. 6 depicts a set of alternate approaches to gather historical sleep data, historical sleep quality indices and historical sleep system settings in accordance with one implementation of the present invention.

Referring to FIG. 6, a set of alternate processes outline different approaches to gather historical sleep data, historical sleep quality indices and historical sleep system settings in accordance with one implementation of the present invention. In a first case, a person using a sleep system decides a threshold question of whether to access a global sleep repository containing sleep data for a larger population of people (602). If a person wants to contribute, the person can decide to submit their own sleep and environment data gathered during sleep to global sleep repository (604). By contributing the sleep information, the data in the global sleep repository remains current and updated with the latest information from the aggregate of people using the information.

Using this information in the global sleep repository, the sleep system then performs sleep trend analysis on global sleep repository thus updating the various sleep quality indices & corresponding expected sleep system settings (606). In practice, the sleep analysis is generally so complex and the data large that a separate sleep trend analysis server 124 as depicted in FIG. 1 is required to incorporate the newly contributed sleep data and recalculate the statistics for sleep system settings, objective and subjective sleep qualities as well as overall sleep quality indices. Once the statistics are calculated, the sleep system accesses and mines the global sleep repository for suggested sleep system settings in view of the person's sleep quality index and sleep goals (608). For example, the sleep system may discover several different sleep system settings that seem appropriate but must somehow determine the most appropriate set of settings for the user by carefully analyzing the sleep data, environmental data and sleep quality index.

In the alternate case, a person may decide not to access the global sleep repository in which case the person instead contributes and uses sleep and environment data gathered during sleep to local sleep repository (610). The local sleep repository generally only includes sleep data and environmental data concerning the particular person and his or her corresponding sleep patterns. In some cases, this is more effective at suggesting sleep system settings as the results are inherently tailored to the individual. Of course, in other cases there is a need for more solutions in order to solve a sleeping issue that may be shared with many other people.

Next, the sleep system uses the local sleep repository information to perform sleep trend analysis and update sleep quality indices and corresponding sleep system settings (612). These sleep system settings and indices are much smaller and generally can be performed directly using the processing capabilities built into the sleep system. To discover the most optimal solution, the sleep system then mines the local sleep repository for suggested sleep system settings in view of user's sleep quality index and sleep goals (614).

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device.

Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with user.

Accordingly, the invention is not limited to the above-described implementations, but instead is defined by the appended claims in light of their full scope of equivalents.

What is claimed is:

1. A computer implemented sleep modification method with instructions to be executed on a processor, the instructions comprising:

receiving a sleep goal that may be achieved through control of an environment near a person;

contributing personal historical sleep information gathered over time into a sleep repository using sleep data from the person indicative of sleep quality along with corresponding historical environmental data and one or more cycles of the sleep architecture for the person;

combining historical sleep information gathered over time from one or more other people into the sleep repository using sleep data from one or more other people indicative of sleep quality along with corresponding environmental data and one or more cycles of sleep architecture for the other people;

correlating environmental data with the sleep quality and sleep architecture for the person using at least the personal historical sleep information for the person as combined with historical sleep information from the one or more other people in the sleep repository;

creating settings that vary at least one environmental condition of the environment over time as it relates to one or more cycles of a sleep architecture for the person as determined by correlating the environmental data with the sleep quality of the person and other people in the sleep repository; and influencing a sleep quality of the person through control of the at least one environmental condition near the person experiencing one or more cycles of the sleep architecture.

2. The computer implemented method of claim 1 wherein the at least one environmental condition is selected from a set of environmental conditions including light and sound.

3. The computer implemented method of claim 1 wherein the sleep quality includes one or more factors selected from a set of factors including: sleep inertia after waking up, sleep debt accumulation, architecture of sleep phases, breathing quality, sleep efficiency, duration of wakeups during sleep time, actual frequency of wakeups, sleep onset time, wake-up time, and total sleeping time and actual time taken to fall asleep.

4. The computer implemented method of claim 3 wherein the sleep quality is measured as a weighted combination of the one or more factors.

5. The computer implemented method of claim 1 wherein the sleep quality for the person is normalized to allow the sleep quality for the person to be compared with a sleep quality from other people.

6. The computer implemented method of claim 1 wherein the sleep quality for the person and corresponding environmental data are normalized to allow for a comparison with a sleep quality from other people and an associated corresponding environmental data.

7. The computer implemented method of claim 1 wherein correlating environmental data with the sleep quality and sleep architecture for the person using at least the personal historical sleep information for the person as combined with historical sleep information from one or more other people in the sleep repository further comprises:

performing sleep trend analysis on personal historical sleep information for the person as combined with the historical sleep information from the one or more other people to update the at least one environmental condition used in the sleep architecture for the person; and mining the personal historical sleep information for the person as combined with the historical sleep information from the one or more other people for one or more suggested environmental conditions in view of the desired sleep goal for the person.

8. A computer implemented sleep modification method to be executed on a processor comprising:

receiving a sleep goal that may be achieved through control of an environment near a person;

contributing personal historical sleep information gathered over time into a sleep repository using sleep data from the person indicative of sleep quality along with corresponding historical environmental data and one or more cycles of the sleep architecture for the person;

combining historical sleep information gathered over time from one or more other people into the sleep repository using sleep data from one or more other people indicative of sleep quality along with corresponding environmental data and one or more cycles of sleep architecture for the one or more other people;

correlating environmental data with the sleep quality and sleep architecture for the person using at least the personal historical sleep information for the person as combined with the historical sleep information from the one or more other people in the sleep repository;

creating settings that vary at least one environmental condition of the environment over time as it relates to one or more cycles of a sleep architecture for the person as determined by correlating the environmental data with the sleep quality of the person and the one or more other people in the sleep repository;

influencing a sleep quality of the person through control of the at least one environmental condition near the person experiencing one or more cycles of the sleep architecture; and adjusting the at least one environmental condition in the vicinity of the person in accordance with at least the personal historical sleep information and the sleep architecture for the person.

9. The computer implemented method of claim 8 wherein the at least one environmental condition is selected from a set of environmental conditions including light and sound.

10. A sleep system comprising:

a processor capable of executing instructions used in controlling an environment surrounding a person to affect a sleep quality for the person;

a memory capable of holding instructions, which when executed cause the processor to receive a sleep goal that may be achieved through control of the environment near the person, contribute personal historical sleep information gathered over time into a sleep repository using sleep data from the person indicative of sleep quality along with corresponding historical environmental data and one or more cycles of the sleep architecture for the person, combine historical sleep information from one or more other people gathered over time into the sleep repository using sleep data from the one or more other people indicative of sleep quality along with corresponding environmental data and one or more cycles of sleep architecture for the other people, correlate environmental data with the sleep quality and sleep architecture for the person using at least the personal historical sleep information for the person as combined with the historical sleep information from the one or more other people in the sleep repository, create settings for the environment that vary at least one environmental condition over time as it relates to one or more cycles of a sleep architecture for the person as determined by correlating the environmental data with the sleep quality of the person and the one or more other people in the sleep repository for the person that relates to a sleep architecture having one or more cycles and influence a sleep quality of the person through control of the at least one environmental condition near the person experiencing one or more cycles of the sleep architecture.

11. The system of claim 10 further comprising a set of one or more sensors wherein the set of one or more sensors may gather sleep data and environmental data useful to further influence the sleep quality for the person.

12. The system of claim 11 wherein the sensors are selected from a set of sensors including: a respiration sensor, a heartbeat sensor, a movement sensor, an air sensor, a light sensor, a sound sensor, a temperature sensor and other environmental sensors.

13. The system of claim 10 wherein the sleep quality includes one or more factors selected from a set of factors including: sleep inertia after waking up, sleep debt accumulation, architecture of sleep phases, breathing quality, sleep efficiency, duration of wakeups during sleep time, actual frequency of wakeups, sleep onset time, wake-up time, and total sleeping time and actual time taken to fall asleep.

14. The system of claim 10 further comprising instructions that normalize the sleep quality for the person allowing the sleep quality for the person to be compared with a sleep quality from other people.

15. The system of claim 10 wherein the one or more different environmental conditions may further include a set of different conditions including: light, temperature, air, sound and vibration.

* * * * *